United States Patent [19]

Oyama et al.

[11] Patent Number: 4,629,535
[45] Date of Patent: Dec. 16, 1986

[54] METHOD FOR DETECTING AN AIR-FUEL RATIO

[75] Inventors: Yoshishige Oyama; Minoru Osuga, both of Katsuta, Japan

[73] Assignee: Hitachi, Ltd., Tokyo, Japan

[21] Appl. No.: 702,750

[22] Filed: Feb. 19, 1985

[30] Foreign Application Priority Data

Feb. 17, 1984 [JP] Japan ................................. 59-27138

[51] Int. Cl.$^4$ ............................................ G01N 27/46
[52] U.S. Cl. .................................... 204/1 T; 204/425; 204/426; 204/427; 204/429
[58] Field of Search .......................... 204/1 S, 421–429

[56] References Cited

U.S. PATENT DOCUMENTS

| | | | |
|---|---|---|---|
| 4,207,159 | 6/1980 | Kimura et al. | 204/425 |
| 4,224,113 | 9/1980 | Kimura et al. | 204/426 |
| 4,264,425 | 4/1981 | Kimura et al. | 204/429 |
| 4,306,957 | 12/1981 | Ishitani et al. | 204/426 |
| 4,440,621 | 4/1984 | Kitahara et al. | 204/425 |

Primary Examiner—T. Tung
Attorney, Agent, or Firm—Antonelli, Terry & Wands

[57] ABSTRACT

An air-fuel ratio detector including an oxygen ion conductive solid electrolyte, first and second electrodes provided on respective sides of the solid electrolyte, a porous diffusion resistor covering the first electrode, and a circuit arrangement for supplying a current between the first and second electrodes. In order to enable a detection of a wide range of air-fuel ratios, the current supplied between the first and second electrodes is controlled so as to feed oxygen from the second electrode to the first electrode through the solid electrolyte and then withdraw oxygen from the first electrode to the second electrode through the solid electrolyte. At the time of withdrawal of the oxygen, the mobility or migration of the oxygen is measured, with the mobility of the oxygen being detected in dependence upon a variation rate of a withdrawal current, an average value of the withdrawal current, or a time period from the starting time of the withdrawal to a time when the oxygen content near the first electrode has become nearly zero.

6 Claims, 34 Drawing Figures

METHOD FOR DETECTING AN AIR-FUEL RATIO

BACKGROUND OF THE INVENTION

The present invention relates to an air-fuel ratio detector and method for detecting an air fuel ratio and, more particularly, to an air-fuel ratio dectector and method for detecting an air fuel ratio of an air fuel mixture supplied to an internal combustion engine.

Air-fuel ratio detectors or oxygen concentration sensors have been proposed wherein electrodes are provided on either side of a bottom of a tubular solid electrolyte formed of, for example, zirconia, with the atmosphere being introduced into an interior of the tubular solid electrolyte, and with an outer side of the tubular solid electrolyte being exposed to the gas to be measured.

In an air-fuel ratio detector of the aforementioned type, an output is produced such that the electromotive force is incrementally changed at a theoretically ideal or optimum air-fuel ratio of, for example, 14.7. For this reason, a detector of the aforementioned type is generally widely employed in control of internal combustion engines for motor vehicles to determine whether the air-fuel mixture supplied to the internal combustion engine is lean or rich relative to the theoretically ideal or optimum air-fuel ratio.

Recently, an air-fuel ratio detector has also been developed for detecting a lean air-fuel ratio so as to burn a lean mixture thereby conserving fuel. For example, in FIGS. 4 and 5 of U.S. Pat. No. 4,282,080, corresponding to Japanese Laid Open Patent Application No. 55-125548, a detector is proposed which comprises a solid electrolyte and a porous diffusion resistor, with a threshhold current being measured so as to detect the lean air-fuel ratio.

Additionally, in FIG. 1A of, for example, U.S. Pat. No. 4,158,166, corresponding to Japanese Patent Laid-Open Application No. 53-66292, a further detector is proposed which includes a solid electrolyte and a single-holed diffusion resistor. In this proposed detector, oxygen is pumped into a reference chamber by a solid electrolyte pump and reacts therein with CO flowing into the reference chamber through the single hole thereby detecting a rich air-fuel ratio.

Furthermore, in U.S. Pat. No. 4,304,652, corresponding to Japanese Laid-Open Patent Application No. 55-166039, a detector is proposed which includes a solid electrolyte and a porous diffusion resistor, with a direction of the current passing the solid electrolyte being selectively reversed so as to determine whether the air-fuel ratio is lean or rich.

In, for example, U.S. Pat. No. 4,272,331, a detector is proposed which includes a pump cell which adds or removes gaseous oxygen from a volume, with a sensor cell being provided for detecting an EMF developed as a result of the pumping action of the pump cell. An external circuit causes a pump current to flow which removes the oxygen from the volume until the EMF reaches a reference voltage. Then, pumping is reversed until the EMF reaches another reference voltage, with the pumping pattern being caused to repeat thereby establishing an oscillatory period that is proportional to the partial pressure of the oxygen.

While each of the above described detectors function in particular ranges, none of the detectors can provide a complete detection over a wide range of the air fuel ratios from a rich to a lean operation.

Accordingly, the aim underlying the present invention essentially resides in providing an air-fuel ratio detector which is capable of detecting a wide range of air-fuel ratios from rich to lean.

In accordance with advantageous features of the present invention, an air-fuel ratio detector is provided which includes an oxygen ion conductive solid electrolyte, first and second electrodes respectively provided on each side of the electrolyte, a diffusion resistor provided on the first electrode and exposed to the measured gas, as well as a means for supplying a current between a first electrode and the second electrode so as to feed oxygen from the second electrode to the first electrode through the solid electrolyte during a predetermined time, and then withdraw oxygen from the first electrode to the second electrode through the solid electrolyte. Additonally, means are provided for measuring the mobility or migration of the oxygen withdrawn from the first electrode to the second electrode through the solid electrolyte.

The mobility of migration of oxygen is detected on the basis of a variation rate of withdrawal current, an average value of the withdrawal current, or a period from the starting time of the withdrawal to the time when oxygen content near the first electrode becomes substantially zero.

In accordance with the present invention, oxygen is intially fed from the second electrode to the first electrode and the partial pressure of the oxygen near the first electrode provides a value which is proportional to the oxygen partial pressure in the measured gas in a lean air-fuel ratio and, in an inverse proportion to the partial pressure of carbon monoxide in the measured gas in a rich air-fuel ratio; therefore, it becomes possible to measure air-fuel ratios ranging from rich to lean.

In accordance with advantageous features of the present invention, the mobility of the oxygen, i.e., the migration of the oxygen ions, is detected in dependence upon a variation rate of current which passes between the second electrode and the first electrode at a beginning of the oxygen withdrawal.

It is also possible in accordance with the present invention to detect the mobility or migration of the oxygen ions based upon an average value of a current which passes between the second electrode and the first electrode during the oxygen withdrawal.

Advantageously, in accordance with further features of the present invention, the mobility of the oxygen, i.e., migration of the oxygen ions, may be detected in dependence upon a period from the starting time of the oxygen withdrawal to a time when the oxygen content near the first electrode reaches a predetermined value which is substantially equal to zero.

Advantageously, it is possible to detect when the oxygen content near the first electrode has become a predetermined value in dependence upon a change in the electromotive force produced between the first electrode and the second electrode.

The second electrode may be exposed to the atmosphere or, alternatively be exposed to the gas to be measured.

In accordance with still further features of the present invention, a diffusion resistor provided on the first electrode and exposed to the measured gas is fashioned as a porous diffusion resistor and, advantageously, the porous diffusion resistor may be covered with a porous protective layer which has a porosity greater than that of the porous diffusion resistor.

In accordance with additional features of the present invention, the diffusion resistor may include at least one cover which defines a chamber and includes an orifice and the solid electrolyte may be porous and serve also as the diffusion resistor.

In accordance with the method of the present invention a current is supplied between the first and second electrodes so as to feed oxygen from the second electrode to the first electrode and enable a withdrawing of oxygen from the first electrode to the second electrode through the solid electrolyte, and measuring a mobility of oxygen ions withdrawn from the first electrode to the second electrode through the solid electrolyte for determining the air fuel ratio.

In accordance with the method of the invention the step of measuring may include detecting a variation rate of current passing between the second electrode and first electrode at a beginning of the oxygen withdrawal.

It is also possible in accordance with the present invention to detect an average value of current passing between the second and first electrode during the oxygen withdrawal.

In accordance with yet further features of the method of the present invention, the measuring step may include detecting a period of time from a starting time of the oxygen withdrawal to a time when the oxygen content near the first electrode has reached a predetermined value substantially equal to zero, with the period of time being detected by, for example, a determining of a change in electromotive force provided between the first and second electrodes.

Accordingly, it is an object of the present invention to provide an air-fuel ratio detector and method of detecting an air fuel ratio which avoids by simple means, shortcomings and disadvantages encountered in the prior art.

Another object of the present invention resides in providing an air-fuel ratio detector which is simple in construction and therefore relatively inexpensive to manufacture.

Another object of the present invention resides in providing an air-fuel ratio detector which provides a complete detection over a wide range of air fuel ratios from rich to lean.

These and other objects, features, and advantages of the present invention will become more apparent from the following description when taken in connection with the accompanying drawings which show, for the purposes of illustration only, several embodiments in accordance with the present invention.

DETAILED DESCRIPTION OF THE DRAWINGS

Figure 1:
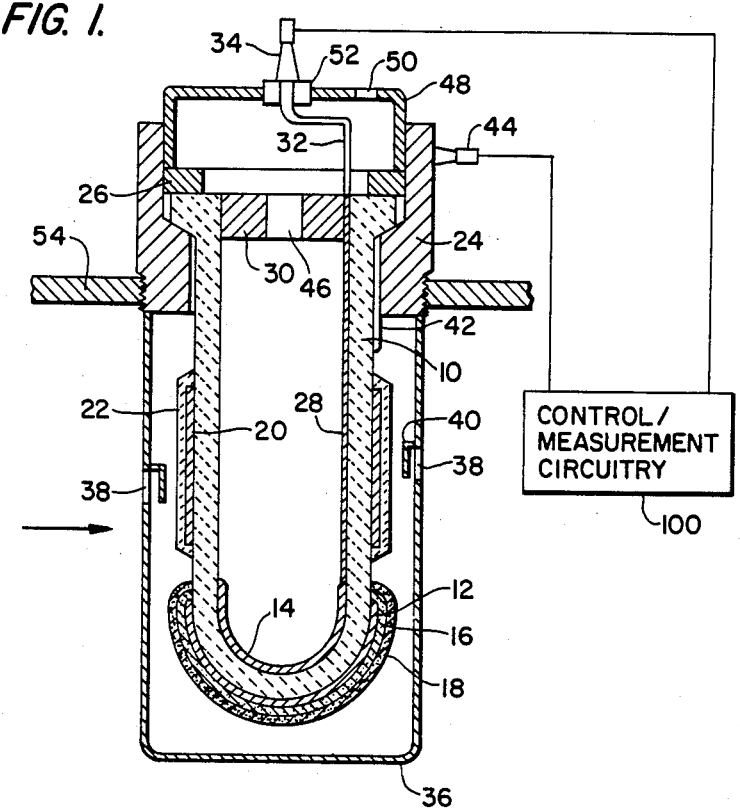
FIG. 1 is a longitudinal cross-sectional view of an air-fuel detector constructed in accordance with the present invention.

Referring now to the drawings wherein like reference numerals are used throughout the various views to designate like parts and, more particularly, to FIG. 1, according to this figure, an oxygen ion conductive solid electrolyte 10 is of a tubular form and is formed of a solid material consisting essentially of, for example, 91% by weight of $ZrO_2$ and 9% by weight of $Y_2O_3$, with the solid electrolyte being about 2 mm thick and having electric resistance of, for example, 33Ω at 800° C. An outer side of the solid electrolye 10 is coated with a first electrode 12 consisting essentially of a porous platinum, with an inner side thereof being coated with a second electrode 14 consisting essentially of porous platinum. The electrodes 12, 14 are formed in such a manner that the platinum paste is applied onto the surface of the electrolyte 10 and baked to a thickness of about 20–200 μm. Advantageously, the platinum paste consists of an organic solvent containing about 15% platinum with a grain size of 0.1 μm.

A porous diffusion resistor 16 is coated on the outer side of the electrode 12, with the resistor being formed of, for example, $MgO$-$Al_2O_3$ spinel and has a thickness of about 10–30 μm; however, the thickness, if necessary, could be greater. The pore volume of the porous diffusion resistor 16 is less than 0.2 cc/g thereby giving rise to a resistance against the oxygen when it travels to reach the electrode 12. A protective layer 18 is coated on the outer side of the porous diffusion resistor 16, with the protective layer being formed of, for example, $Al_2O_3$ powder and having a thickness of 50–100 μm. The pore volume of the protective layer 18 is larger than the pore volume of the porous diffusion resistor 16, for example, greater than 0.2 cc/g.

A heater 20, formed, for example, of a platinum film, is provided at a portion of the electrolyte 10, with an outer side of the heater 20 being coated with a dense glass ceramic protective layer 22. A metal fitting or coupling 24 is attached to the end of the electrolyte 10 so as to fix the same together with a metal retainer 26. A lead film 28 for the electrode 14 is extended along the inner side of the electrolyte 10 up to the inner end thereof thereby comming into contact with the metal retainer 30. A lead wire 32, connected to the metal retainer 30, is, in turn, connected to a terminal 34, with a cover 36 being fixed to the metal fitting 24 to protect the electrolyte 10. A plurality of ports 38 are formed in a portion of the cover 36, with a deflector 40 being provided near the ports 38 to prevent exhaust gas from directly striking the electrolyte 10.

The electrode 12 is connected to the metal fitting 24 through a lead film 42 and is further connected to the terminal 44, with openings 46, 50 being respectively formed in the metal retainer 30 and a metal retainer 48 of the terminal 32 to enable an introduction of the atmosphere. An insulating member 52 insulates the terminals 32, 44 from each other, with the metal fitting 24 being fixed, for example, to an exhaust pipe 54 of an internal combustion engine. The terminals 32, 44 are both connected to a control measurement circuitry 100 which is adapted to control the voltage or current applied between the electrodes 12, 14 and measure the air-fuel ratio of the exhaust gas. Terminals (not shown) for the heater 20 are provided in a similar manner to the terminals for the electrodes 12, 14.

The air-fuel ratio detector illustrated in FIG. 1 operates in the following manner:

The air-fuel ratio is measured by the steps of first feeding oxygen to the side of the first electrode 12 from the side of the second electrode 14 and then withdrawing the oxygen from the side of the first electrode 12 to the side of the second electrode 14.

Figure 2:
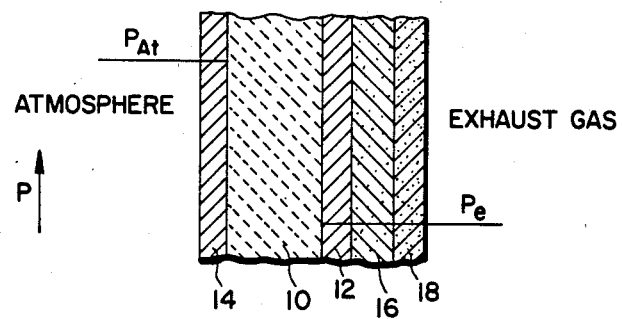
FIG. 2 is a partial cross-sectional view, on an enlarged scale, of a portion of the detector of FIG. 1.

As shown most clearly in FIG. 2, which is a distal end of the solid electrolyte 10 of FIG. 1, the left side of FIG. 2 corresponds to the interior of the tubular electrolyte 10 into which atmosphere is introduced. The oxygen partial pressure of the atmosphere is assumed to be $P_{At}$. A right side of FIG. 2 corresponds to the exterior of the electrolyte 10 which is exposed to the exhaust gas. The oxygen partial pressure of the exhaust gas is assummed to be $P_e$ and, FIG. 2, represents the oxygen partial pressure in the respective components with neither voltage nor current being applied between the electrodes 12, 14. More particularly, an interior of the porous electrode 14 has the same oxygen partial pressure $P_{At}$ as the atmosphere, and the oxygen partial pressure in the electrode 12, diffusion resistor 16, and protective layer 18 equals that of the exhaust gas, that is, $P_e$.

A current of, for example, 30 mA is then caused to pass between the electrodes 12, 14 so that the oxygen in the atmosphere is reduced to oxygen ions at the inner face between the electrode 14 and the electrolyte 10, with the oxygen ions being transferred through the electrolyte 10 and being oxidized into oxygen molecules at the interface with the electrode 12 thereby causing the oxygen to be fed from the side of the electrode 14 to the side of the electrode 12. At the beginning of the feeding of the oxygen, an equilibrium state shown in FIG. 2, the oxygen partial pressure in the electrode 12 is gradually increased and, consequently, the oxygen partial pressure in the diffusion resistor 16 varies.

Figure 3:
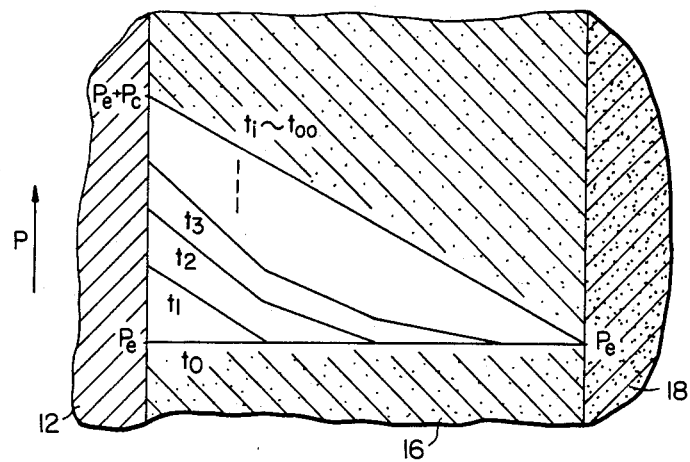
FIG. 3 is a diagramatic view illustrating variations in a partial pressure of oxygen at the time of oxygen feeding.

More particularly, as shown in FIG. 3, a solid line at time $t_o$ represents the state prior to the starting of the oxygen feeding step, where the electrode 12, diffusion resistor 16, and protective layer 18 all have the same oxygen partial pressure $P_e$. Thereafter, as shown by the solid line $t_1$, $t_2$, and $t_3$ in FIG. 3, the oxygen partial pressure in the diffusion resistor 16 is increased; however, the oxygen partial pressure in the protective layer 18 is always maintained at $P_e$ of the exhaust gas since the protective layer 18 has a greater porosity. At the expiration of a given time period $T_i$ the oxygen partial pressure at the interface between the diffusion resistor 16 and the electrode 12 comes into a balanced state and has a value of $P_e + P_c$ greater than the oxygen partial pressure $P_e$ of the exhaust gas by a given amount $P_c$. After that, even if the oxygen is further fed in any amount, the oxygen is all discharged into the exhaust gas through the diffusion resistor 16 and the protective layer 18.

Figure 4:
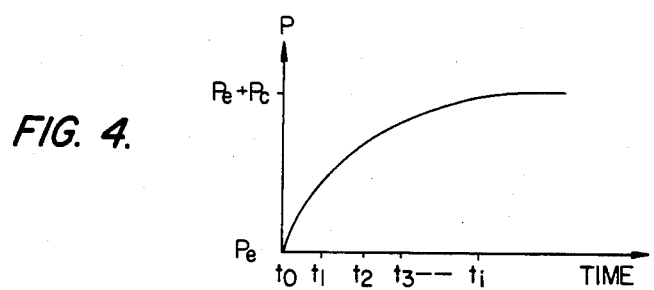
FIG. 4 is a graphical illustration of variations in the partial pressure of the oxygen with respect to time at the time of oxygen feeding.

A variation of the oxygen partial pressure with respect to time at the interface between the diffusion resistor and the electrode 12 is illustrated in FIG. 4. More particularly, in FIG. 4, a predetermined amount $P_c$ is determined by the resistance k of the diffusion resistor 16 in a current $I_o$ passing between the electrodes 12, 14. In otherwords, the given amount $P_c$ is expressed by the relationship $k.I_o$. Assuming that the diffusion resistor 16 has a thickness of 100 μm and a pore volume of 0.1 cc/g and also assuming that the current $I_o$ of 30 mA is passed therethrough, the predetermined or given amount $P_c$ corresponding to an increase in oxygen is equal to about 3%. The time $t_1$ required to reach the balance state is about 2 ms, with the time $t_1$ being different in dependence upon the oxygen partial pressure at the interface between the diffusion resistor 16 and the electrode 12 at the time $T_0$. More specifically, assuming that the oxygen partial pressure at the interface is zero at the time $t_0$ and the oxygen partial pressure $P_e$ of the exhaust gas is 3%, the interface oxygen partial pressure reaches a balanced state at the time that it is increased up to 6% after a lapse of, for example, 4 ms.

After the oxygen partial pressure at the interface between the diffusion resistor 16 and the electrode 12 has been increased by the amount $P_c$ relative to the oxygen partial pressure $P_e$ of the exhaust gas thereby reaching a balanced state as described above, the oxygen on the side of the electrode 12 is then withdrawn to the side of the electrode 14. To this end, a given voltage is applied between the electrodes 12, 14 of an opposite polarity to that for supplying the current during the oxygen feeding step thereby causing the oxygen partial pressure in the diffusion resistor 16 to be gradually reduced.

Figure 5:
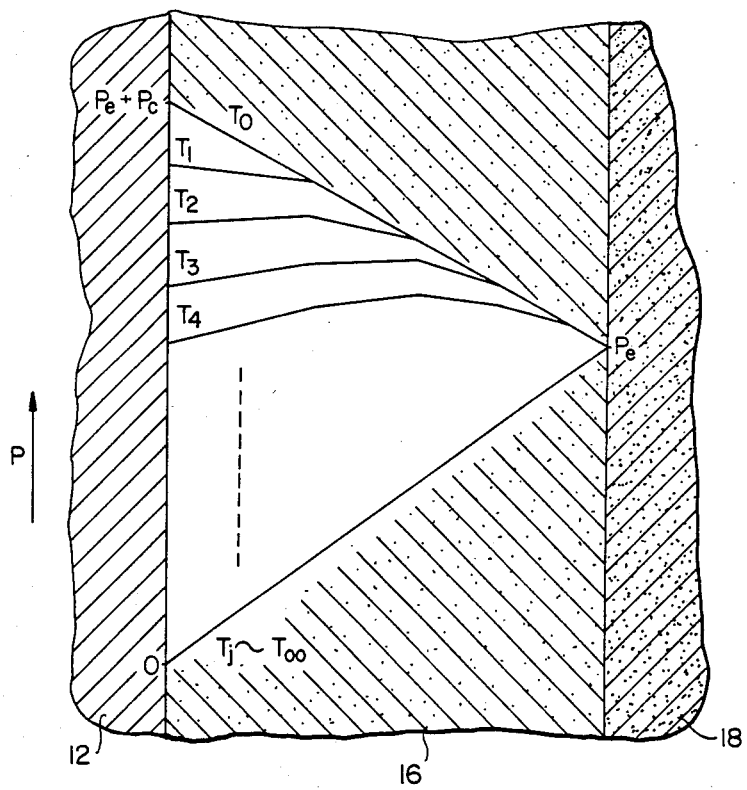
FIG. 5 is a diagramatic view illustrating variations of the partial pressure of the oxygen at the time of oxygen withdrawal.
Figure 6:
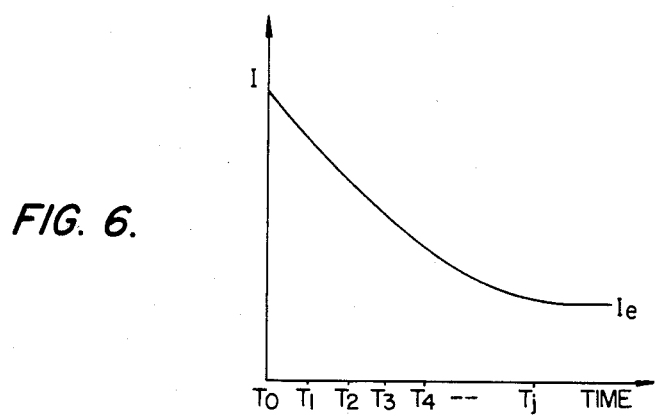
FIG. 6 is a graphical illustration of the variations of current verses time at the time of oxygen withdrawal.

The variations of the oxygen partial pressure in the above descriped step is more clearly depicted in FIG. 5. More particularly, in FIG. 5, a solid line at the time $T_0$ represents the state prior to starting the oxygen withdrawal step where the interface oxygen partial pressure is balance with the higher value by a given amount $P_c$ relative to the oxygen partial pressure $P_e$ of the exhaust gas. Thereafter, as illustrated by the solid lines $T_1$, $T_2$, and $T_3$, the oxygen partial pressure in the diffusion resistor 16 is reduced and, after a lapse of a given period of time $T_j$, the oxygen partial pressure at the interface between the diffusion resistor 16 and the electrode 12 becomes zero. After that, the oxygen partial pressure at the interface is maintained at zero or, in other words, the oxygen in the exhaust gas diffusing through the diffusion resistor 16 is all pumped out to the side of the electrode 14 from the side of the electrode 12 through the electrolyte 10. During the oxygen withdrawal step, the current I passing between the electrodes 12, 14 is, as shown most clearly in FIG. 6, varied with the current I being gradually reduced from the time $T_0$ to $T_j$ and, after the time period $T_j$, a constant $I_e$ passes therebetween, with the current $I_e$ representing a threshhold current.

Figure 7:
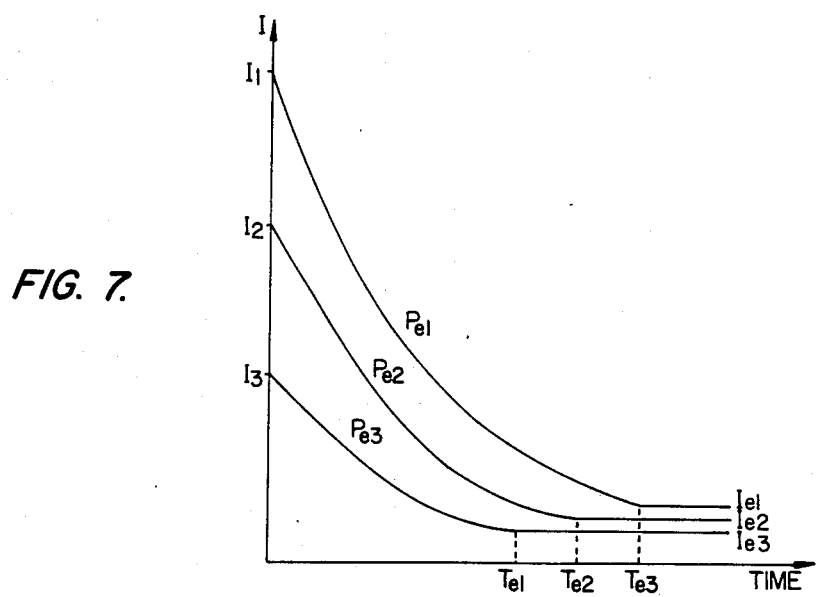
FIG. 7 is a graphical illustration of the relationship of the current with respect to time during different partial pressure of the oxygen.

The amount of the current I is dependent upon the oxygen partial pressure of the exhaust gas or, more particularly, as shown in FIG. 7, the starting current is changed as indicated by the solid line curves $I_1$, $I_2$ or $I_3$ in accordance with the oxygen partial pressure $P_{e1}$, $P_{e2}$ or $P_{e3}$, respectively. The threshhold current also varies or is different as indicated by $I_{e1}$, $I_{e2}$ or $I_{e3}$, respectively. Similarily, the time when the threshhold current appears differs as indicated by the time periods $T_{e1}$, $T_{e2}$ or $T_{e3}$, respectively.

Figure 8A:
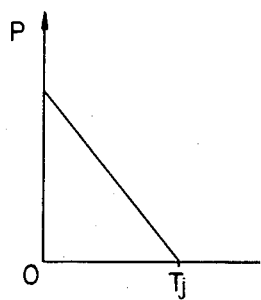
FIGS. 8A and 8B are graphical illustrations of the relationship between the partial pressure and the electromotive force.
Figure 8B:
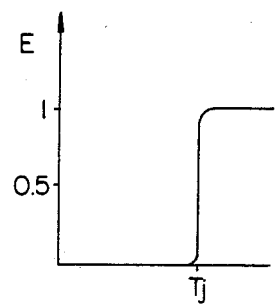

The oxygen partial pressure at the interface between the electrode and the diffusion resistor 16 during the oxygen withdrawal step is gradually reduced and, as shown in FIG. 8A then becomes zero at the time period $T_j$. Measuring the electromotive force E between both the electrodes 12, 14 during that time period, indicates that the electromotive force changes rapidly from 0V to 1V at the time $T_j$ as shown most clearly in FIG. 8B. Therefore, it is possible to determine the time $T_j$ based on a change in the electromotive force E. As a result of studying the relationship between the oxygen partial pressure of the exhaust gas, that is, the air-fuel ratio (A/F), and the time $T_j$, it has been determined that a linear relationship exists between A/F and T from a rich mixture wherein A/F is less than the theoretical air-fuel ratio (A/F:14.7) to a lean mixture where A/F is greater than that value as shown most clearly in FIG. 9. Consequently, the air-fuel ratio can be measured by determining the time T.

In a rich mixture, the exhaust gas contains carbon monoxide rather than oxygen and the partial pressure of the carbon monoxide increases linearly as the air-fuel ratio decreases; therefore, a rich air-fuel ratio can be measured by determining the partial pressure of the carbon monoxide. When oxygen is fed to the side of the electrode 12, provided that the partial pressure of the carbon monoxide in the exhaust gas is $P_e(CO)$, the oxygen partial pressure at the interface between the electrode 12 and the diffusion resistor 16 reaches a balance state where it is assumed to be $P_e(CO)+P_c(O_2)$, as shown most clearly in FIG. 10. For example, assuming that $P_e(CO)$ is 2% and $P_c(O_2)$ is 3%, the oxygen partial pressure at the interface becomes 2% since the oxygen reacts with the carbon monoxide in accordance with the following relationship:

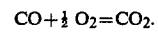

$$CO + \tfrac{1}{2} O_2 = CO_2.$$

Figure 9:
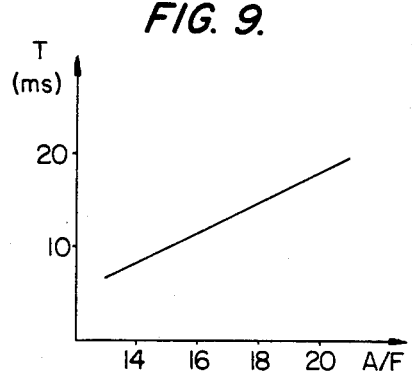
FIG. 9 is a graphical illustration of the relationship between the time when the electromotive force is produced and an air-fuel ratio.
Figure 10:
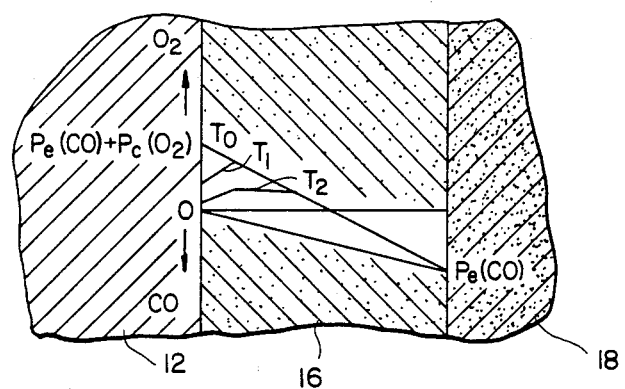
FIG. 10 is an illustration depicting variations of the partial pressure of the oxygen in a rich air-fuel ratio.

When the oxygen is withdrawn, the oxygen partial pressure in the diffusion resistor 16 varies in the manner indicated by the solid lines $T_0$, $T_1$ and $T_2$ in FIG. 10. Consequently, the period of time during which the oxygen partial pressure at the interface is zero represents the partial pressure of the carbon monoxide and, therefore, the air-fuel ratio. A change in the partial pressure of carbon monoxide per unit of air-fuel ratio in a rich mixture is twice that in the oxygen partial pressure per unit of the air-fuel ratio in a lean mixture so that there also exists a linear relationship between the time T and the air-fuel ratio A/F as shown most clearly in FIG. 9.

Figure 11:
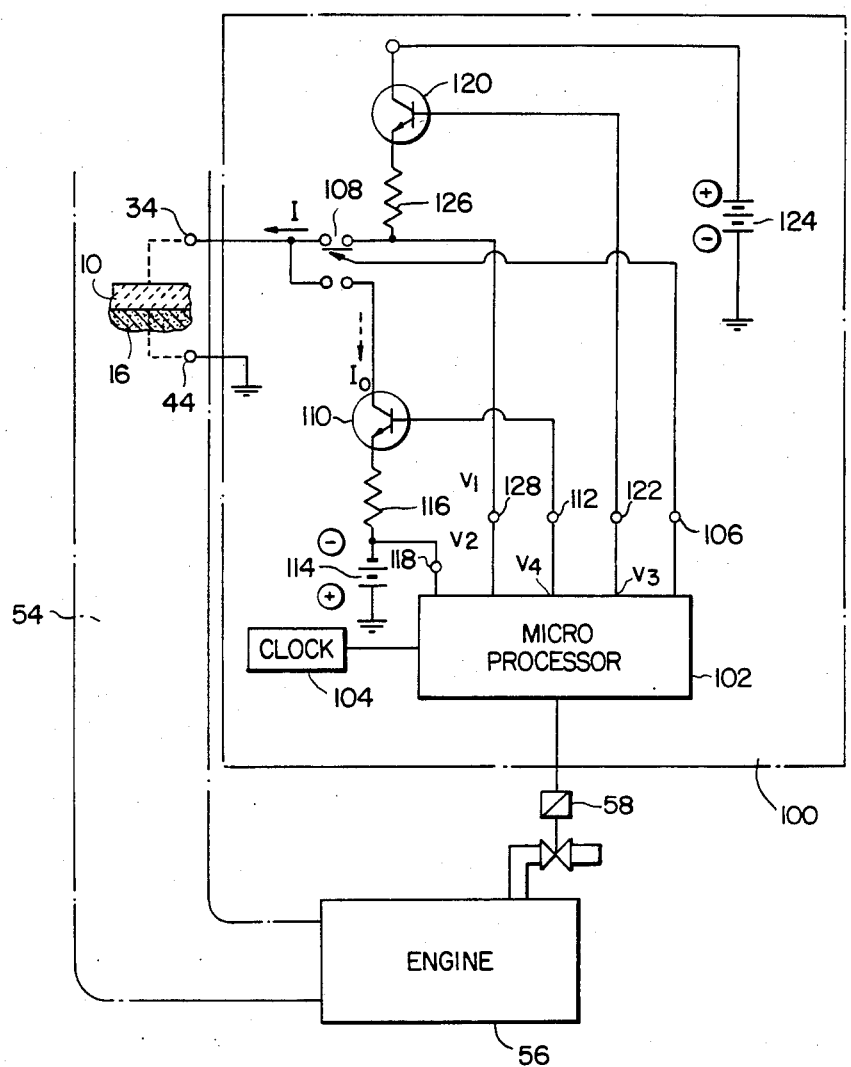
FIG. 11 is a circuit diagram of a control/measuring arrangement for an air-fuel ration detector constructed in accordance with the present invention.

In order to measure the time T, as shown most clearly in FIG. 11, a control measurement circuit 100 is provided. The air-fuel ratio detector or sensor includes a solid electrolyte 10 and a diffusion resistor 16 having a construction similar to FIG. 1, with the detector being installed in a gas passage 54 connected to a downstream side of a combustor 56 for an internal combustion engine, or the like. The terminals 34, 44 of the sensor section are connected to the control measurement circuit 100, with a main portion of the circuit 100 including a microprocessor 102 for controlling the device in accordance with a program stored therein which program may, for example, correspond to the flow diagram illustrated in FIG. 12 of the drawings. The microprocessor 102 executes a program in synchronism with signals from a clock 104 and is adapted to change over a relay 108 to close an upper switch thereof or to close a lower switch thereof with a signal issued to a terminal 106 of the microprocessor 102.

When a lower switch of the relay 108 is in a closed state or closed position, a certain current $I_o$ is passed between the electrodes on both sides of the electrolyte 10 to feed oxygen. A transistor 110 is operated at a voltage $V_4$ at terminal 112 of the microprocessor 102. When the transistor 110 is conductive, the current is supplied from a power source 114 to produce a voltage $V_2$ through a detection resistor 116, which voltage is applied to the processor 102 from a terminal 118.

When the upper switch of the relay 108 is closed, it is possible to apply a voltage to withdraw oxygen, and a transistor 120 is operated with a voltage $V_3$ at a terminal 122 of the processor 102. When the transistor 120 conducts, the voltage is applied from a power source 124, and a current I passing during the oxygen withdrawal step is detected through a detection resistor 126 and taken into the processor in the form of a voltage $V_1$ from a terminal 128, with the voltage $V_1$ also being used for detecting electromotive force between the electrodes. As also shown in FIG. 11, the combustor 56 is provided with a fuel adjusting valve 58 which is adapted to be opened and closed under the control of the microprocessor 102.

Figure 12:
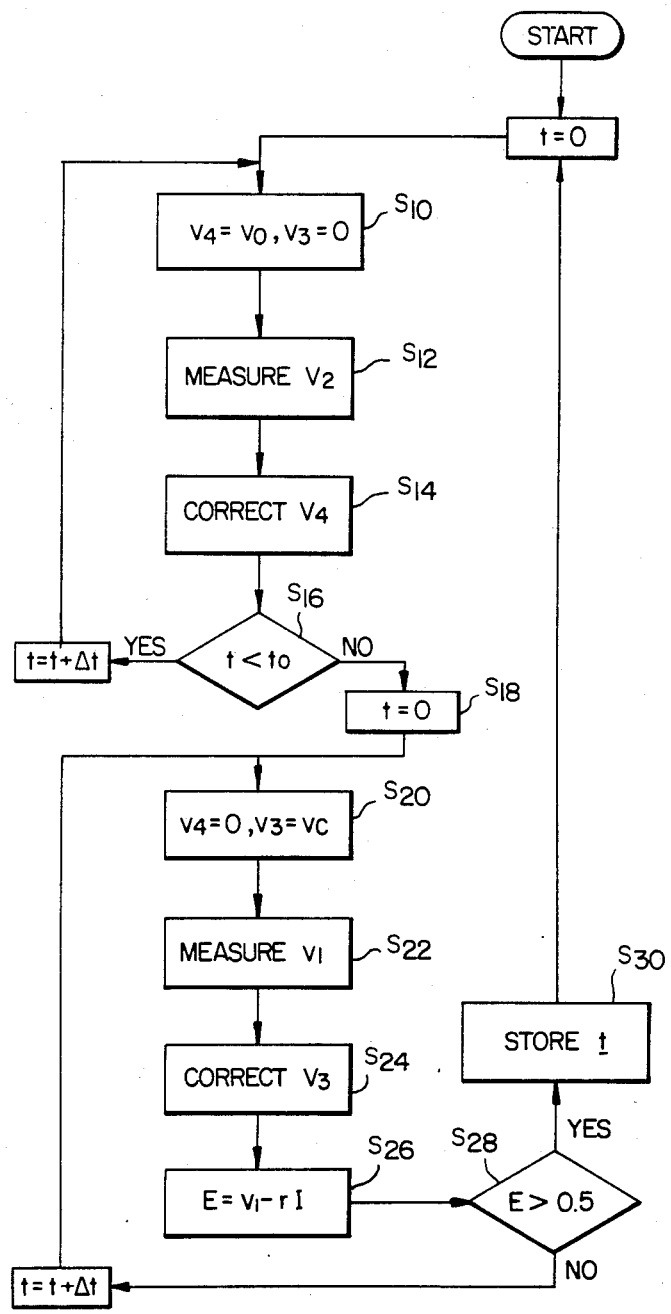
FIG. 12 is a flow diagram illustrating the operation of the circuitry of FIG. 11.

The operation of the above-described arrangement is as follows:

As shown most clearly in FIG. 12, in step $S_{10}$, the microprocessor 102 outputs $V_4=V_0$ and $V_3=0$. Thus, the transistor 120 is interrupted and the transistor 110 conducts. In step $S_{12}$, a signal $V_2$ is measured or taken in, and in step $S_{14}$, $V_4$ is corrected so that the signal $V_2$ becomes constant, that is, that the current of, for example, 30 mA becomes constant. As a result of a decision in step $S_{16}$, if the time t is less than a predetermined time of, for example, 10 ms, the steps $S_{10}$–$S_{14}$ are repeated or, in other words, a certain current $I_o$ is passed for 10 ms to feed oxygen into the diffusion resistor. If the time exceeds 25 ms, the time t counted in a counter is cleared to zero in step $S_{18}$, and in step $S_{20}$, the microprocessor 120 then sets $V_4=0$ and $V_3=V_c$. Namely, the transistor 110 is interrupted and the transistor 120 conducts. In step $S_{22}$, $V_1$ is measured and $V_3$ is corrected in ste $S_{24}$ so that the signal $V_1$ becomes constant, that is, that the current I becomes constant. In step $S_{26}$, the electromotive force E between the electrodes is determined through calculations of $V_1-rI$, wherein r represents and internal resistance of the solid electrolyte, that is, a known value. In step $S_{28}$ it is determined whether or not the electromotive force E exceed 0.5 V and, if the electromagnetic force E exceeds 0.5 V, steps $S_{20}$–$S_{26}$ are repeatedly continued. If the electromotive force E exceeds 0.5, the value of t is stored in step $S_{30}$ and the microprocessor 102 returns to step $S_{10}$ after clearing the time t to 0.

Figure 13:
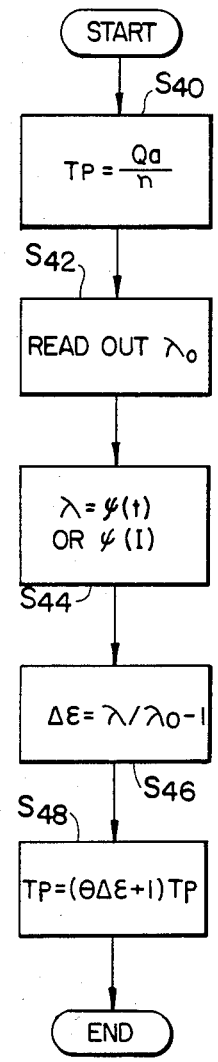
FIG. 13 is a flow diagram illustrating the step for determining a fuel injection amount.

FIG. 13 provides a flow diagram of a program built into the microprocessor 102. More particularly, in step $S_{40}$, a basic fuel injection amount $T_p$ is determined in dependence upon both the intake air amount $Q_a$ detected by an air flow sensor (not shown) and a rotational speed n detected by a crank angle sensor (not shown). In step $S_{42}$, the particular air excess rate $\lambda_0$ determined from the operating conditions such as, for example, rotational speed n, amount of intake air $Q_a$ and intake air temperature is read out of a map of air excess rates $\lambda_0$ (air-fuel ratios $(A/F)_0$) which are prestored in a RAM of the microprocessor 102. In step $S_{44}$, the actual air excess rate (air-fuel ratio (A/F)) is then determined based on the time t temporarily stored in the step $S_{30}$. In step $S_{46}$, the measured air excess rate (air-fuel ratio (A/F)) is compared with a target air excess rate $\lambda_0$ (air-fuel ratio $(A/F)_0$) to determine a deviation $\Delta\epsilon$. The air fuel injection amount $T_p$ is corrected in step $S_{48}$ using the deviation $\theta\Delta\epsilon$ and, in the step $S_{48}$, with $\theta$ representing a proportional constant.

By virtue of the above-noted features of the present invention, it is possible to measure the air-fuel ratios ranging from rich to lean mixtures.

Figure 14:
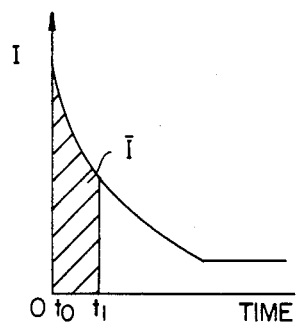
FIGS. 14 and 15 are graphical illustrations of the relationship between average values of the withdrawal current and air-fuel ratios.
Figure 15:
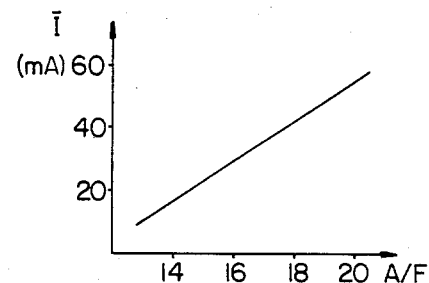
Figure 16:
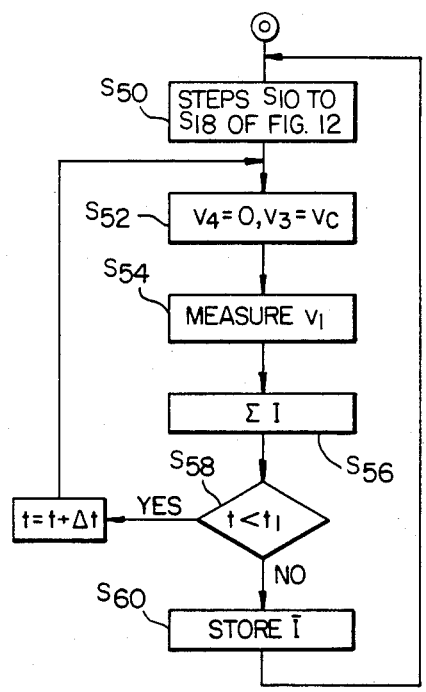
FIG. 16 is a flow diagram illustrating the operation of another embodiment of a flow detector constructed in accordance with the present invention.

FIGS. 14–16 represent another embodiment of the present invention wherein a current passing, during the step of withdrawing oxygen, after feeding oxygen into the diffusion resistor 16 to bring the oxygen partial pressure at the interface between the diffusion resistor 16 and the electrode into a balanced state where it is higher than the oxygen partial pressure of the exhaust gas by a predetermined or given value, is varied in the manner shown in FIGS. 7 or 14. Upon measuring an average value I for a predetermined time period ($t_1$) such as, for example, 5 ms, after starting to withdraw oxygen, it has been determined that there exists a linear relationship between the average current value I and the air-fuel ratio A/F, clearly illustrated in FIG. 15. In this connection, the expression average value I means an integrated value of the current I in a range of a time period $T_0$ to $T_1$ which is indicated in the hatched area in FIG. 14, or, in the alternative, the actual average value thereof in a range from $t_0$ to $t_1$.

In the embodiment of FIGS. 14–16, the control measurement circuit 100 has the same constructional components as that shown in FIG. 11 and as shown most clearly in FIG. 16, in the step $S_{50}$, the microprocessor 102 implements the step of feeding oxygen similar to the steps $S_{10}$–$S_{18}$ in FIG. 12 and, after a completion of the feeding of oxygen, the microprocessor 102 sets $V_4=0$ and $V_3=V_c$ in step $S_{52}$, where $V_c$ is a constant set at, for example, 0.5 V. Next, $V_1$ is measured in step $S_{54}$ and, at this time, since the electromotive force E=0, the oxygen withdrawal current I can be measured based on $V_1$, with the current value I then being integrated in step $S_{56}$. As a result of the decision in step $S_{58}$, if the time t is less than a predetermined time $t_1$ of, for example, 5 ms, the steps $S_{52}$–$S_{56}$ are repeated and, if the time t is greater than 5 ms, the integrated value of the current I until that time is stored as an average value $\bar{I}$ in step $S_{60}$. The average value I is used in calculating the actual air excess rate illustrated in step $S_{44}$ in FIG. 13.

Figure 17:
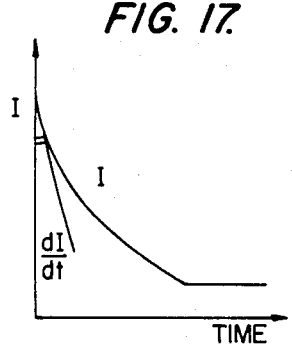
FIGS. 17 and 18 are graphical illustrations of the relationship between the variaton rate of withdrawal current and air fuel ratios.

FIG. 17 provides an example of yet another embodiment of the present invention wherein, in the illustrated embodiment, the variation rate of current during the oxygen withdrawing step is taken into account. More particularly, the current I during oxygen withdrawing is varied as shown in FIG. 17 and, as a result of a measuring of a time differential value dI/dt of the current I, that is, a variation rate of the current, just after starting to withdraw the oxygen with respect to the air-fuel ratios A/F, it has been determined that a linear relationship exists therebetween as shown most clearly in FIG. 18.

Figure 19:
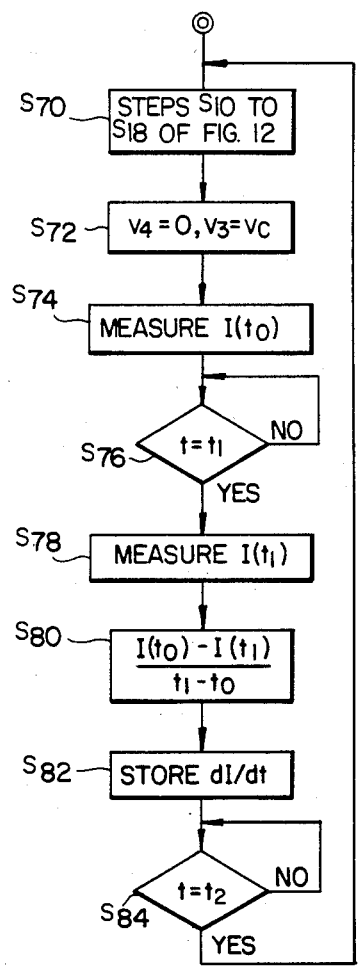
FIG. 19 is a flow diagram illustrating the operation in yet another embodiment of an air-fuel ratio detector constructed in accordance with the present invention.

The operation of the embodiment of FIG. 17 is best understood by referring to the flow diagram of FIG. 19 and, as with the previous embodiments, the control measurement circuit 100 has the same construction or components as that shown in FIG. 11. More particularly, in step $S_{70}$, the microprocessor 102 implements the step of feeding oxygen similar to the steps $S_{10}$–$S_{18}$ in FIG. 12 and, after a completion of the oxygen feeding, the microprocessor 102 sets $V_4=0$ and $V_3=V_c$ in step $S_{72}$ thereby starting to withdraw the oxygen, where $V_c$ is constant at, for example, 0.5 V. Next, in step $S_{74}$ the current $I(t_0)$ which passes at the time $T_0$ of starting to withdraw oxygen as measured and it is then monitored in step $S_{76}$ until the time t exceeds a predetermined time ($t_1$ such as, for example, 1 ms). After the lapse of the predetermined time $t_1$, the current I passing at that time $t_1$ is measured in step $S_{78}$. Next, the value of dI/dt is calculated in step $S_{80}$, with the calculation being based on the following relationship:

$$(I(t_0)-I(t_1))/(t_1-t_0).$$

The resultant value of $dI/d_t$ from the above relationship is then stored in $S_{82}$ and, subsequently, oxygen is continuously withdrawn until the time t exceeds a predetermined time $t_2$ such as, for example, 5 ms. After a lapse of a time period $t_2$, the microporcessor 102 returns to the first step $S_{70}$.

Figure 18:
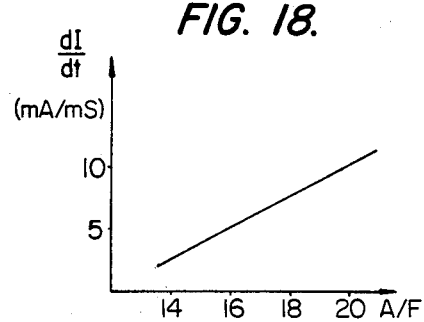

The oxygen feeding time and oxygen withdrawing time in connection with the measurement of the time period T in FIG. 9, as well as the measurement of the average current $\bar{I}$ in FIG. 15, as well as the measurement of the current variation rate dI/dt in FIG. 18 will now be described.

In, for example, FIG. 5, the oxygen withdrawing time is $T_j$ at a maximum and, in the case of measuring the time T in FIG. 9, the maximum time $T_j$ is measured. Assuming that the controlled air-fuel ratio is 20 at a maximum in the control of an internal combustion engine, the oxygen content of the exhaust gas is about 6% in this situation. More particularly, $P_e$ is 6% and, when the oxygen is withdrawn under these circumstances with $P_c$ being equal to 3%, the required time is about 6 ms. This value is dependent upon the value of $P_c$, that is, the diffusion resistance k determined by the porsity and the thickness of the resistor 16, the diffusion feeding current Io, and the withdrawing current I. In other words, the time $T_j$ is approximately 10 ms and, when measuring the time period $T_j$ in this manner, the measured result may be affected by dust adhering to the solid electrolyte 16. Thus, it is preferable to continue to make measurements until the time $T_4$ with the diffusion resistor 16 on a side near the electrode 12 rather than making measurements until the time $T_j$ in FIG. 5. In this connection, the measurement of the average current I can be made for about the half time, that is, for example, about 5 ms. The measurement of dI/dt can be made for a much shorter period of time, but it is preferable to withdraw oxygen for about 5 ms also in this situation, and this results from taking into account a reduction of the oxygen partial pressure of the exhaust gas.

As to a consideration of the oxygen feeding time, assuming that the oxygen partial pressure at the interface is equal to zero and $P_e$ is equal to 6% during a measuring of $T_j$, an oxygen partial pressure of 9% is required to reach a balanced state. The time required to provide such an oxygen partial pressure is 6 ms. Assuming that the withdrawing time is 5 ms in the case of measuring the current I the required feeding time can further be shortened because the oxygen partial pressure at the interface is greater than zero.

In other words, a period of about 10 ms is enough to respectively feed and withdraw oxygen and the total period of 20 ms is sufficiently short to enable a controlling of an internal combustion engine.

In comparison with the previously proposed methods for measuring threshold current, the present invention is less susceptible to the effects of dust and also, while the value of the threshold current is several mA at maximum, the initial current in the step of withdrawing oxygen reaches several times 10 mA in accordance with the present invention thereby resulting in an increasing in the accuracy when measuring of the values of the current I and dI/dt.

Figure 20:
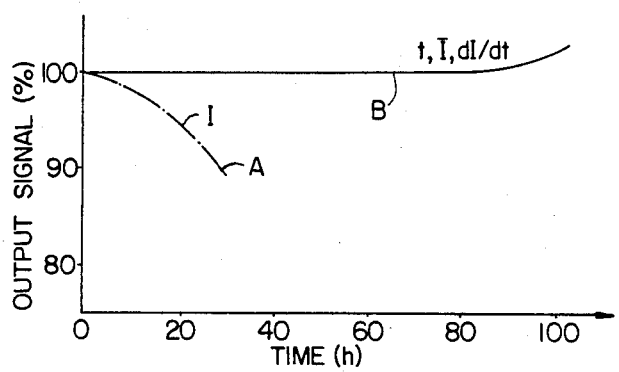
FIG. 20 is a graphical illustration depicting the relationship between time-dependent variations of an output signal of an air-fuel ratio detector.

FIG. 20 provides an example of time dependent variations of an output signal from an air-fuel ratio detector and, more particularly, according to this figure, an output signal A is obtained with a conventional detector such as, for example, a detector disclosed in U.S. Pat. No. 4,282,080, with an output signal B being obtained from a detector constructed in accordance with the present invention.

The previously proposed detector arrangement is arranged just to withdraw oxygen in the exhaust gas with a solid electrolyte, with the oxygen diffusing through the diffusion resistor, and with the oxygen content of the exhaust gas being measured based on the threshold current which flows during an oxygen withdrawal. On this occassion, the value of the threshold current varies in dependence upon the resistance value of the diffusion resistor and, if dust in the exhaust gas adheres to the surface of the diffusion resistor in contact with the exhaust gas, the resistance of such a dust adhering area would be increased. The resistance value within the diffusion resistor would remain unchanged and would be less than the dust adhering portion. Consequently, the limit current value is determined by the resistance value of the dust adhering portion and, for example, if dust adheres to the surface of the diffusion resistor and its resistance value is doulbed, the limit current value would be reduced by one-half.

Figure 21:
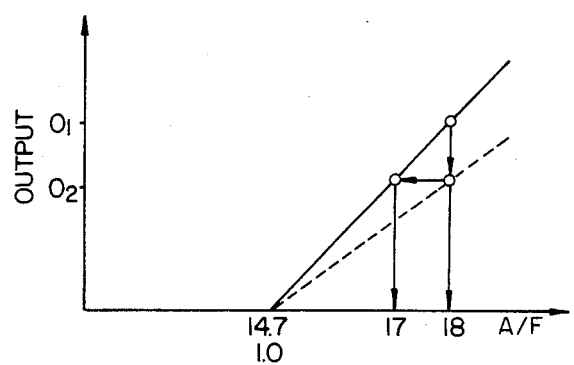
FIG. 21 is a graphical illustration depicting the relationship between the outputs and air-fuel ratios of air-fuel ratio detectors constructed in accordance with the prior art.

Furthermore, because the output signal is gradually reduced with the lapse of time in the conventional detector, a problem arises in a misfiring of an engine when the detector is employed as a control arrangement for an internal combustion engine. More particularly, assuming that a conventional detector has an output characteristic such as shown by the solid line in FIG. 21, and further assuming that the characteristic is changed to be gradually reduced with a lapse of time as indicated by the broken line in FIG. 21, when the control unit is arranged to maintain the air-fuel ratio at, for example, 18, the output of the detector is reduced to the level $0_2$ from the original level $0_1$ and, in this case, the control unit determines that the air-fuel ratio at that time is 17 thereby reducing the supply of the amount of fuel so that the air fuel ratio is held at 18. Consequently, the mixture becomes too lean to ignite and the internal combustion engine stops.

Figure 22:
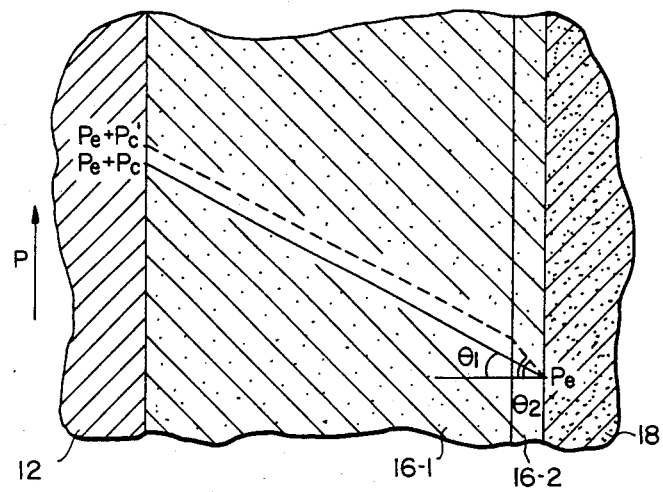
FIG. 22 is a view illustrating an influence of the air-fuel ratio detector during a predetermined lapse of time for an embodiment constructed in accordance with the present invention.

The effect of dust adhering onto the surface of the diffusion resistor 16 is relatively small in accordance with the contruction of the present invention as indicated by the output signal B in FIG. 20 as compared with previously proposed conventional detectors. Furthermore, since the effect of the dust increases the level of the output signal, it will never be accompanied by the problems relating to misfiring when the detector is employed for an internal combustion engine. More particularly, FIG. 22 provides a graphical illustration of the influence of the effects of adhering dust with respect to a lapse of a predetermined time period. In FIG. 22, the solid line corresponds to a situation wherein the oxygen partial pressure reaches a balance state at a time $t_i$ in FIG. 3, that is, a situation wherein the diffusion resistance will not be changed over a predetermined lapse of time. Conversely, the dotted line represent a balanced state of the oxygen partial pressure when the time dependent changes are included. Stated differently, the portion of the diffusion resistor 16-1 has an unchanged resistance value; whereas, the portion of the diffusion resistor 16-2 has an increased resistance value due to the adhering dust. Assuming that the resistance is doubled due to the adhering dust, the angle $\theta_2$ is twice the angle $\theta_1$ as apparent from FIG. 22. As noted hereinabove, the given amount $P_c$ in a balanced state is expressed by $k \cdot I_o$, when, without adhering dust, where, k is the diffusion resistance value, and $I_o$ is the current value. Meanwhile, when adhering dust is present, assuming that the resistance value of the portion 16-2 in which the resistance value of the diffusion resistor 16 which has been changed due to adhering dust is 2k, and that the entire diffusion resistor 16 is occupied by the portion 16-2 at a proportion x, the amount $P_{c'}$ in a balanced state is expressed by the following relationship:

$$Pc' = k \cdot (1-x) \cdot Io + 2k \cdot x \cdot Io = k \cdot (1+x) \cdot Io$$

If the thickness of the diffusion resistor 16 is assumed to be 100 μm, the portion undergoing changes in resistance due to the adhering dust has a thickness of 1 μm to 5 μm. When the thickness is 1 μm, the portion x is equal to 0.01 so that $P_{c'}$ is increased by about 1% relative to $P_c$. Even when the thickness is 5 μm, $P_{c'}$ is increased by only 5% relative to the $P_c$. In previously proposed conventional detectors, if the diffusion resistance is doubled, the level of the output signal is reduced by half. In accordance with the present invention, the level of the output signal is increased by only 1%–5%; therefore, the present invention provides superior results over previously proposed detectors. Furthermore, in contradistinction to previously proposed conventional detectors, in accordance with the present invention, the output signal increases with the time-dependent changes thereby ensuring a prevention of a problem of misfiring when the detector is applied to an internal combustion engine.

The above described time dependent changes can be calibrated in the following manner. More particularly, the fuel adjusting valve 58 of the combustor 56 in FIG. 11 is temporarily interrupted in its operation so that the gas passage 54 only contains air therein. At that time, the oxygen partial pressure is constant at, for example, 21%, so that an output signal $\bar{I}_c$ in such a situation is measured and the resultant value is utilized to calibrate the time-dependent changes. The output signal $\bar{I}$ is expressed by the following equation, where the diffusion resistance k is a variable:

$$\bar{I} = Io + Pe/k.$$

If the signal I at the time $P_e$ has a value of 0.21 and such signal is assumed to be $\bar{I}_c$, k is expressed by the following relationship:

$$k = 0.21/(\bar{I}_c - Io).$$

Figure 23:
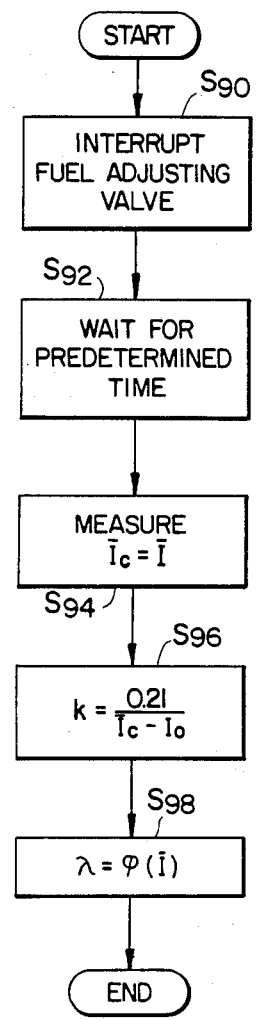
FIG. 23 is a flow diagram illustrating a calibration method of time-dependent changes.

Consequently, the value of k can be determined by measuring $\bar{I}_c$. The calibration of the time-dependent changes may be performed in accordance with the flow diagram shown in FIG. 23.

More particularly, the microprocessor 102 interrupts the fuel adjusting valve 58 in the step $S_{90}$ and waits for a lapse of a predetermined time period so that a space around the electrolyte 10 is filled with air. In such a state, the signal $\bar{I}$ is measured in step $S_{94}$, and measurement of the signal $\bar{I}$ is carried out in accordance with the flow diagram illustrated in FIG. 16. Then, the resultant $\bar{I}$ is assumed to be $\bar{I}_c$ and, in step $S_{96}$, the changed diffusion resistance k is calculated using the foregoing equation. Thereafter, in step $S_{98}$, the relationship of $\lambda = \phi(I)$, that is, the relationship between the air-fuel ratio A/F (air excess rate $\lambda$) and the signal $\bar{I}$ is corrected.

It is also noted that the time-dependent changes can be calibrated in a similar manner using the signal t or dI/dt, in addition to the signal $\bar{I}$.

As apparent from the above description, the effect of the time-dependent change is slight even without including the protective layer 18; however, the overall advantageous effects can be further increased by utilizing the protective layer 18 to trap dust and, consequently, it is preferable to provide a protective layer 18.

Figure 24:
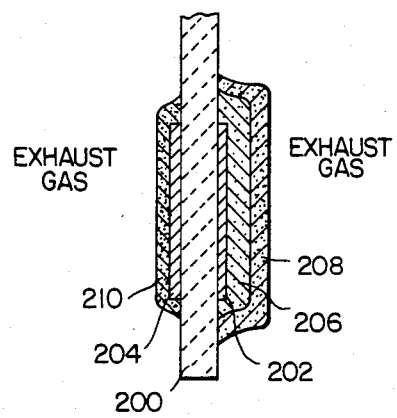
FIGS. 24–28 are partial cross-sectional views of still a further air-fuel ratio detector constructed in accordance with the present invention.
Figure 25:
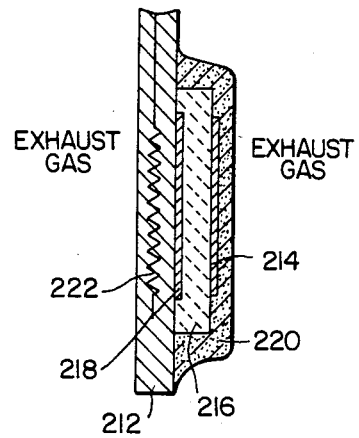
Figure 26:
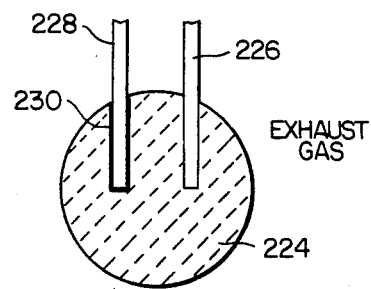
Figure 27:
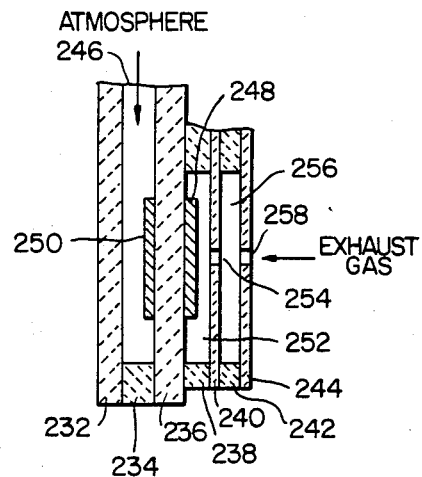
Figure 28:
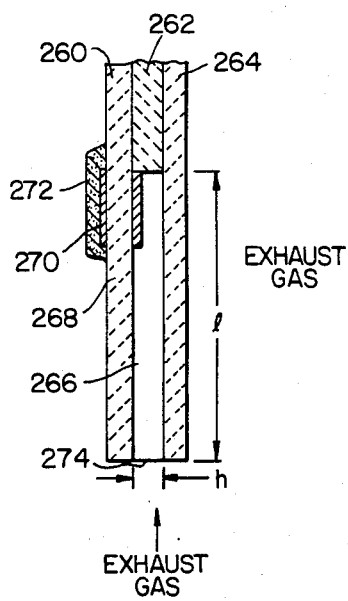

As can readily be appreciated, the sensor section employed in the present invention is not limited to the sensor construction illustrated in FIG. 1 and, for example, the sensor section may take other possible constructions such as, for example, the constructions illustrated in FIGS. 24–26 wherein the sensor sections are arranged so that both the electrodes are exposed to the exhaust gas instead of exposing either one of them to the atmosphere. The embodiments illustrated in FIGS. 27 and 28 are arranged so that a single-holed diffusion resistor is employed in place of the porous diffusion resistor.

Referring now to FIG. 24, a platinum paste is applied onto both sides of a zirconia substrate 200 ($ZrO_2$: 92% by weight, $Y_2O_3$: 8% by weight) with a thickness of 400 μm, and then baked to form electrodes 202, 204. A diffusion resistor 206 is coated on the electrode 202, with the diffusion resistor 206 being formed of MgO-$Al_2O_3$ spinel and has a thickness of about 200 μm. A pore volume is about 0.1 cc/g. The diffusion resistor 206 is, in turn, coated with a protective layer 208 and, the electrode 204 is also coated with a protective layer 210 with a pore volume of each of the protective layers 208, 210 being larger than 0.2 cc/g. The porosity of the electrode 204 is also comparable to that of the protective layers 208, 210.

The embodiment of FIG. 24 is operated through the steps of first feeding oxygen from the electrode 204 to the side of the electrode 202 and then withdrawing the oxygen from the side of the electrode 202 to the side of the electrode 204. Consequently, such a sensor is entirely exposed to the exhaust gas without employing any reference oxygen source such as the atmosphere; however the exhaust gas contains oxygen in a small amount of oxygen exists even in a region less than the theoretical air/fuel ratio, so that oxygen can be employed as an oxygen source.

In the embodiment of FIG. 24, during the step of withdrawing oxygen, oxygen resides in the electrode 204 and the protective layer 210. The less the oxygen content of the exhaust gas, the less the amount of oxygen residing therein; therefore, the amount of oxygen to be fed into the side of the electrode 202 in the next cycle is also reduced, and then the zironica substrate 200 enters a conductive state. For this reason, it is necessary that the oxygen in the exhaust gas be fed more easily and, this may be accomplished by selecting the diffusion resistance of the electrode 204, the protective layer 210, etc., so as to be less than that of the diffusion resistor 206.

In the embodiment of FIG. 25, an electrode 218 is formed on an alumina substrate 212 with a thickness of 1 mm with platinum paste. An electrolyte 216, of a thickness of 100 μm–300 μm is formed on the electrode 218 with a plasma jet. The electrolyte consists essentially of $ZrO_2$ in the range of 90–94% by weight and $Yb_2O_3$ of about 6–10% by weight. An electrode 214 is provided on the electrolyte 216, with the electrode 214 being formed of a platinum paste, which is coated with a protective layer 220 on the outer side thereof. The electrolyte 216 is porous and also serves as a diffusion resistor. Additionally, a heater 222 is built into the alumina substrate 222. The sensor arrangement of FIG. 25 is operated in the same manner as that of FIG. 24.

In FIG. 26, a pair of platinum electrodes 226, 228 each having a diameter of 0.4 mm are built in parellel with a spacing of two millimeters therebetween into a pellet-like porous electrolyte 224 which is about 3 mm in diameter and about 1.9 mm in thickness. The electrolyte 224 is formed of $ZrO_2$ stabilized with $Y_2O_3$ and has a porosity of 22%. In the embodiment of FIG. 26, oxygen is first fed from the electrode 228 toward the electrode 226 so that the oxygen content around the electrode 226 comes into a balanced state where it is higher than the oxygen content of the exhaust gas and then the direction of current is reversed to withdraw the oxygen. In this connection, a coating 230 of gold is provided on the outer peripheral surface of the electrode 228 to prevent the reaction of oxygen with carbon monoxide thereby making it possible to avoid a reduction in the oxygen content near the electrode 228 even in a rich mixture where the air-fuel ratio is less than the theoretically ideal ratio. Stated in a different manner, even in a rich mixture where the air-fuel ratio is less than the theoretical ideal, a sufficient amount of oxygen can be supplied to the space around the electrode 226.

In FIG. 27, seven laminated green sheets 232–244 are provided, with each of the sheets being formed of $ZrO_2$ stabilized with $Y_2O_3$ the green sheet 234 is provided with a groove 246 which serves as a communication hole with the atmosphere. The groove 246 can be formed in such a manner that an organic binder is packed into the portion which will later become the groove and then burnt out at the time of a sintering of the green sheet 234. Electrodes 248, 250 are each provided on either side of the green sheet 236 by printing, with the green sheet 238 functioning to provide a first chamber 252. The green sheet 240 is provided with a first orifice 254 which serves as a diffusion resistor, and the green sheet 242 functions to provide a second chamber 256. The green sheet 244 is provided with a second orifice 258 which serves as a diffusion resistor. The first chamber 252 has a volume of 3 $mm^3$, with the second chamber 256 having a volume of 6 $mm^3$. Each of the orifices 254, 258 have a diameter of 0.3 mm and the green sheets each have a thickness of 100 $\mu$m–400 $\mu$m.

In the embodiment of FIG. 27, oxygen is supplied to both chambers 252 and 256 so that the oxygen partial pressure in the chamber 256 reaches a balanced state where it is higher than the oxygen partial pressure $P_e$ of the exhaust gas by a value of $k_1 \cdot I_0$, and the oxygen partial pressure in the chamber 252 comes into a balanced state where it is higher than the oxygen partial pressure in the chamber 256 by a value of $k_2 \cdot I_0$, with $k_1$, $k_2$ respectively representing diffusion resistances of the orifices 258, 254. The oxygen partial pressure of the exhaust gas is then measured by withdrawing oxygen from the chamber 252.

The embodiment of FIG. 28 is formed by three laminated green sheets 260–264, with each of the green sheets 260–264 being formed of $ZrO_2$ stabilized with $Y_2O_3$. A groove 266 is formed in a manner similar to the groove 246 in the construction of FIG. 27, and electrodes 268, 270 are respectively provided on either side of the green sheet 260. The electrode 270 is coated with a protective layer 272. The groove 266 has a height h of 200 $\mu$m, a width of 1 mm, and a length of 20 mm, with one end 274 of the groove 266 being opened to the exhaust gas, and with the groove 266 itself functioning as a diffusion resistor.

Figure 29A:
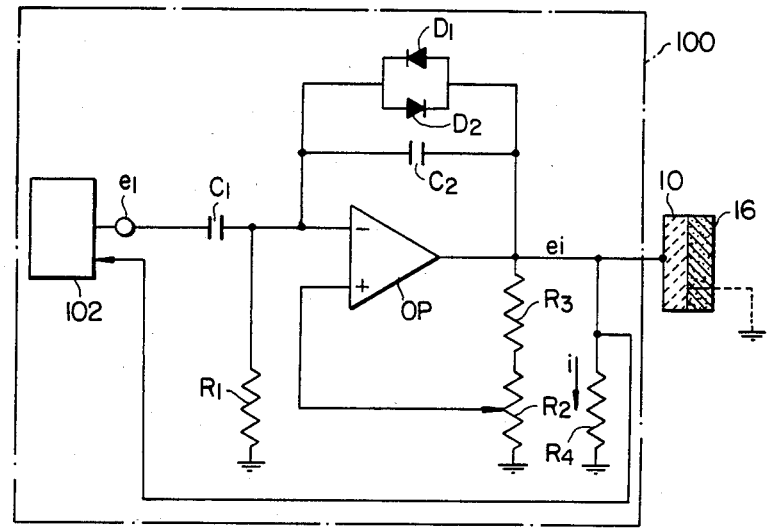
FIG. 29A is a circuit diagram of a control measurement circuitry constructed in accordance with the present invention.
Figure 29B:
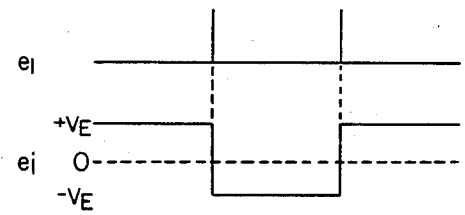
FIG. 29B is a time chart illustrating the operation of the circuitry of FIG. 29A.

As shown in FIGS. 29A and 29B, the control-measurement circuitry 100 may be arranged so that, with a terminal $e_1$ undergoing no input, a positive feedback signal is supplied to a non-inverted input terminal of an operational amplifier OP from an output terminal thereof in accordance with a ratio of resistance $R_2$ to resistance $R_3$, and the output voltage $e_i$ of the amplifier is held at a positive potential while being clipped with the diodes $D_1$, $D_2$. As shown in FIG. 29B, when a pulse signal is applied to the terminal $e_1$ in such an equilibrium state, the output voltage $e_i$ is inverted in its polarity to a negative potential. In this respect, a square wave, a pulse or sine wave can be applied as a signal to the input terminal $e_1$ and, when a pulse is applied to the input terminal $e_1$ with the voltage $e_i$ being in a negative state, the output voltage $e_i$ returns to the original positive state. In other words, the steps of feeding and withdrawing oxygen in the sensor section can be controlled with a trigger signal from a microprocessor 102. The current i during the step of withdrawing oxygen is measured through a detection resistor $R_4$ and then taken into the microprocessor 102 and, upon this occurring, the values of t, dI/dt, I, etc. are then determined.

Figure 30:
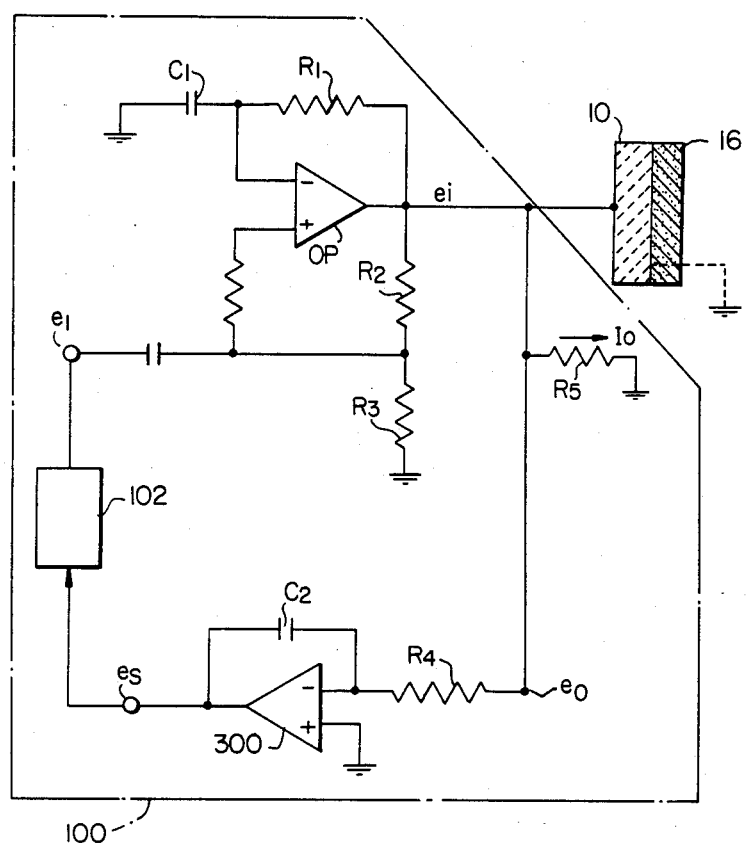
FIG. 30 is a circuit diagram for a control measurement circuitry for an air-fuel ratio detector constructed in accordance with still another embodiment of the present invention.

In the control-measurement circuitry 100 of FIG. 30, when a pulse signal is applied to an input terminal $e_1$, the saturated voltage $+V_E$ of an operational amplifier OP is issued as an output signal $e_i$. The current $I_o$ which passes upon the input of the voltage $e_i$ to the sensor section is detected in the form of a voltage $e_0$, which average value $e_s$ is obtained by an integrator 300 and then taken into the microprocessor 102, with the average value $e_s$ being determined in accordance with the following relationship:

$$e_s = - \frac{1}{C_2 R_4} \int e_i dt$$

The value of $e_s$ is proportional to the air excess rate (air-fuel ratio A/F).

Figure 31:
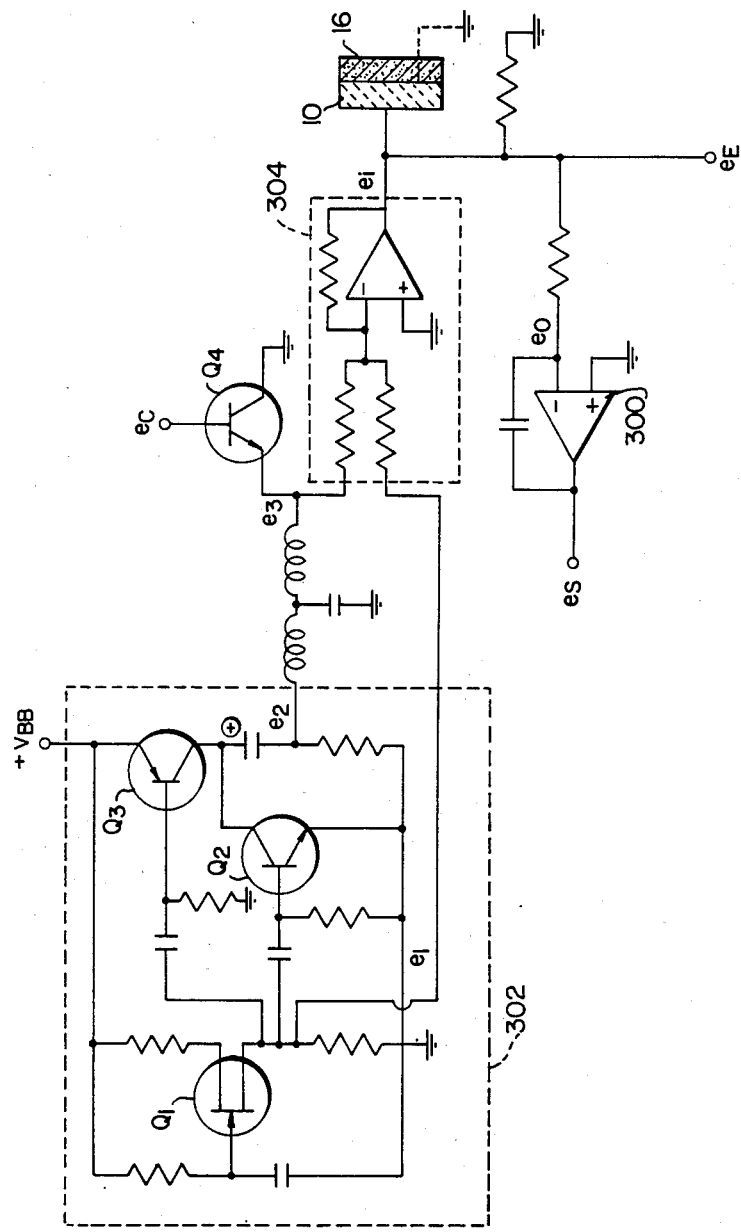
FIG. 31 is a circuit diagram of a control measurement circuitry for an air-fuel ratio detector constructed in accordance with yet another embodiment of the present invention.

As shown in FIG. 31, a circuit 302 serves as a circuit for generating positive and negative pulses employing transistors $Q_1$, $Q_2$ and $Q_3$. More particularly, positive and negative output pulses $e_1$, $e_2$ are produced from a positive DC power source $+V_{BB}$. The transistor $Q_1$ produces a positive pulse $e_1$, while the transistors $Q_2$ and $Q_3$ produce the negative pulse $e_2$ of an opposite phase. An output $e_3$ is produced when the negative pulse $e_2$ is applied to a delay circuit for delaying $e_2$ to an extent of time t.

Figure 32:
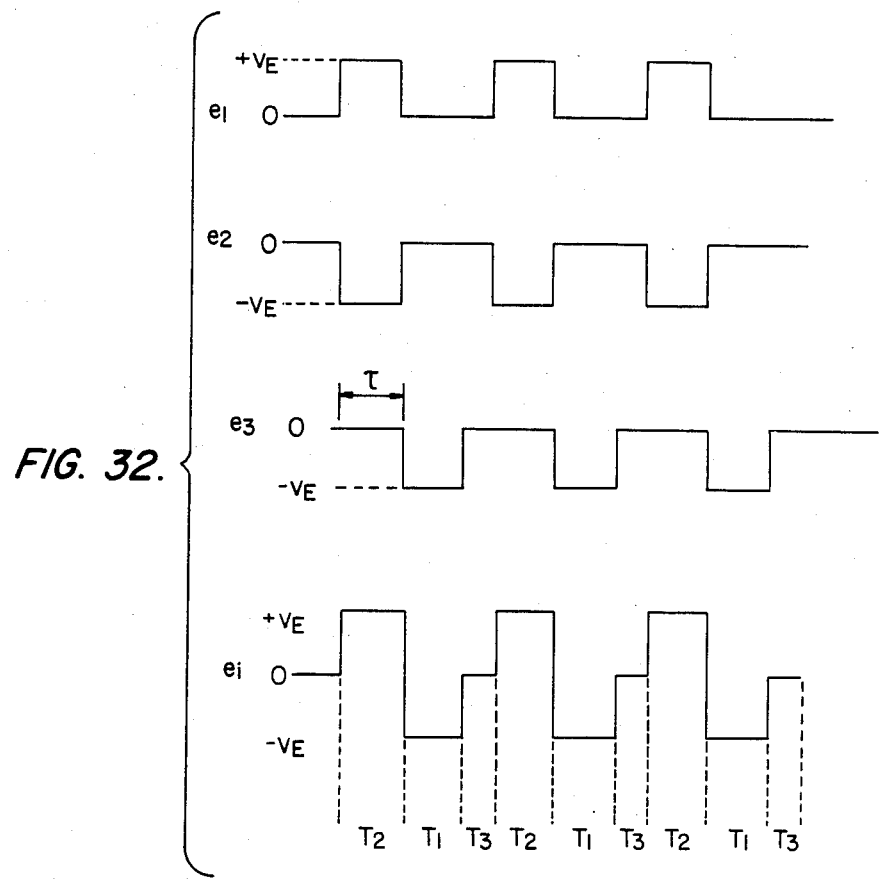
FIG. 32 is a time chart for explaining an operation of the circuitry in FIG. 31.

As evident from FIG. 32 illustrating the wave forms at the respective parts, a combined output $e_i$ of both signals $e_1$ and $e_3$ is obtained by an adder 304. In the waveform of $e_i$, the period $T_1$ is utilized for feeding oxygen and the period $T_2$ is utilized for withdrawing oxygen. During a time period $T_3$, the applied voltage becomes zero and it is determined whether the current air-fuel ratio is leaner or richer than the theoretically ideal air-fuel ratio by measuring the electromotive force produced between both electrodes. If the air-fuel ratio is lean, a voltage $e_c$ is applied to a transistor $Q_4$ for blocking an input of the voltage $e_3$ to the adder 304. If the air-fuel ratio is rich, the voltage $e_3$ is allowed to enter the adder 304 for feeding oxygen thereby preventing the sensor section from coming into an electron conductive region.

Consequently, in accordance with the advantageous features of the present invention, it becomes possible to measure air-fuel ratios ranging from rich to lean.

While we have shown and described several embodiments in accordance with the present invention, it is understood that the same is not limited thereto but is susceptible of numerous changes and modifications as known to one having ordinary skill in the art, and we therefore do not wish to be limited to the details shown and described herein, but intend to cover all such modifications as are encompassed by the scope of the appended claims.

We claim:

1. A method of detecting an air-fuel ratio in an air-fuel ratio detector comprising an oxygen ion conductive solid electrolyte, first and second electrodes provided on respective sides of the solid electrolyte, and a diffusion resistor provided on the first electrode and exposed to a gas to be measured, the method comprising the steps of:

first supplying a current from the first electrode to the second electrode for a first predetermined time so as to feed a predetermined amount of oxygen from the second electrode to the first electrode through the solid electrolyte regardless of the rich to lean air fuel ratios of the gas to be measured;

second supplying a current from the second electrode to the first electrode for a second predetermined time so as to withdraw oxygen from the first electrode to the second electrode through the solid electrolyte regardless of air-fuel ratios from rich to lean of the gas to be measured;

detecting a signal during said second current supplying step representing an amount of oxygen withdrawn from the first electrode to the second electrode through the solid electrolyte until a partial pressure of the oxygen at the interface between the first electrode and the diffusion resistor reaches substantially zero and determining the air fuel ratio of the gas to be measured based on a predetermined relationship between the signal obtained in said detecting step and the air-fuel ratios.

2. A method according to claim 1, wherein the signal in said detecting step is a variation rate of current passing from the second electrode to the first electrode at the beginning of the oxygen withdrawal in said second current supplying step.

3. A method according to claim 1, wherein the signal in said detecting step is an average value of current passing between said second electrode to the first electrode during the oxygen withdrawal in said second supplying step.

4. A method according to claim 1, wherein the signal in said detecting step is a period of time from a starting time of the oxygen withdrawal to a time when the oxygen content near the first electrode has reached a predetermined value substantially equal to zero.

5. A method according to claim 4, further comprising a step of detecting a change in electromotive force appearing between the first and second electrodes in said second current supplying step.

6. A method of detecting an air-fuel ratio of an air fuel mixture with an air-fuel ratio detector comprising an oxygen ion conductive solid electrolyte, first and second electrodes provided on respective sides of the solid electrolyte, the second electrode being exposed to an atmosphere, and a difusion resistor provided on the first electrode and exposed to and exhaust gas, the method comprising the steps of:

feeding oxygen from the second electrode to the first electrode until a partial pressure of the oxygen at the interface between the first electrode and the diffusion resistor reaches a balanced state regardless of air-fuel ratios from rich to lean of the air-fuel mixture;

supplying a predetermined amount of current from the second electrode to the first electrode until a predetermined amount of electromotive force appears between the first electrode and the second electrode so as to withdraw oxygen from the first electrode until a partial pressure of the oxygen at the interface between the first electrode and diffusion resistor reaches substantially zero regardless of air-fuel ratios from rich to lean of the air-fuel mixture;

detecting a period of time from the start of said current supplying step to the appearance of the predetermined amount of electromotive force; and determining the air-fuel ratios of the air-fuel mixture based on a predetermined relationship between the times period obtained in said detecting step and the air-fuel ratios.

* * * * *